United States Patent [19]

Tanikawa et al.

[11] Patent Number: 5,750,523
[45] Date of Patent: May 12, 1998

[54] PYRIDAZINONE DERIVATIVES

[75] Inventors: Keizo Tanikawa; Takashi Matsumoto; Hiroo Matsumoto, all of Funabashi; Nobutomo Tsuruzoe; Hitoshi Nakabeppu, both of Shiraoka-machi, all of Japan

[73] Assignee: Nissan Chemical Industries, Ltd., Tokyo, Japan

[21] Appl. No.: 676,227

[22] PCT Filed: Jan. 24, 1995

[86] PCT No.: PCT/JP95/00069

§ 371 Date: Jul. 23, 1996

§ 102(e) Date: Jul. 23, 1996

[87] PCT Pub. No.: WO95/19969

PCT Pub. Date: Jul. 27, 1995

[30] Foreign Application Priority Data

Jan. 25, 1994 [JP] Japan .................................. 6-006541

[51] Int. Cl.⁶ .................................................. A61K 31/50
[52] U.S. Cl. ........................ 514/247; 514/252; 544/238; 544/240
[58] Field of Search ............................ 544/240; 514/247

[56] References Cited

U.S. PATENT DOCUMENTS

| | | | |
|---|---|---|---|
| 4,783,462 | 11/1988 | Mutsukado et al. | 544/239 |
| 4,892,947 | 1/1990 | Mutsukado et al. | 544/241 |
| 4,978,665 | 12/1990 | Tanikawa et al. | 544/241 |
| 5,011,839 | 4/1991 | Tanikawa et al. | 544/239 |
| 5,098,900 | 3/1992 | Mutsukado et al. | 544/239 |
| 5,202,323 | 4/1993 | Tanikawa et al. | 544/240 |
| 5,219,854 | 6/1993 | Nakashima et al. | 514/247 |
| 5,314,883 | 5/1994 | Tanikawa et al. | 544/238 |
| 5,318,968 | 6/1994 | Tanikawa et al. | 544/238 |

*Primary Examiner*—Donald G. Daus
*Attorney, Agent, or Firm*—Oblon, Spivak, McClelland, Maier & Neustadt, P.C.

[57] ABSTRACT

Pyridazinone derivatives represented by the formula (I) and antiplatelet agents containing them:

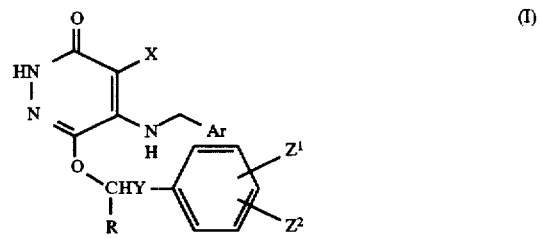

(I)

[wherein R is a hydrogen atom or a $C_1$-$C_4$ alkyl group, X is a hydrogen atom, a chlorine atom or a bromine atom, Ar is a pyridyl group or a phenyl group substituted with $OR^1$ (wherein $R^1$ is a hydrogen atom or a $C_1$-$C_4$ alkyl group) and A {wherein A is a hydrogen atom, a halogen atom, a $C_1$-$C_4$ alkyl group or $OR^2$ (wherein $R^2$ is a hydrogen atom or a $C_1$-$C_4$ alkyl group)}, is $C_1$-$C_8$ alkylene wherein one carbon atom on the straight chain is substituted with one $OR^1$ group (wherein $R^1$ is the same as defined above), and $Z^1$ and $Z^2$ are independently a hydrogen atom, a halogen atom, a $C_1$-$C_4$ alkyl group or a $OR^1$ group (wherein $R^1$ is the same as defined above)].

These compounds have strong antiplatelet effects, are excellently safe, and can be used as active ingredients of prophylactic and therapeutic drugs for various thrombotic diseases.

9 Claims, No Drawings

PYRIDAZINONE DERIVATIVES

TECHNICAL FIELD

This application is a 371 of PCT/JP95/00069 of Jan. 24, 1995.

The present invention relates to novel 3(2H)-pyridazinone derivatives and their salts having an antiplatelet action and pharmaceutical compositions containing them as active ingredients.

BACKGROUND TECHNIQUE

It is known that platelet aggregation plays an important role in thrombus formation, in connection with a disease state. Main thrombotic diseases caused by thrombus formation include cerebral thrombosis, pulmonary thrombosis, myocardial infarction, angina pectoris, occlusion of peripheral arteries and the like, and all of these diseases require development of useful drugs. As a prophylactic or therapeutic drug, an antiplatelet agent having an inhibitory action on platelet aggregation draws public attention. Heretofore, the effect of aspirin has been widely studied, and more recently ticlopidine and cilostazol have been clinically developed. However, they are not active enough or do not act selectively enough. Therefore, a more strongly effective drug is demanded.

In addition to the above-mentioned various thrombotic diseases, various diseases are enumerated as related to platelets. Examples of these diseases include nephritis, cancer cell metastasis and the like, and recently various studies have been conducted with regard to prophylactic or therapeutic effects mainly on these diseases of an antiplatelet agent having an action of controlling the function of the platelet ("Journal of Royal College of Physicians", Vol. 7, No. 1, pp. 5–18, 1972; "Japan Clinics (Nihon Rinsho)", Vol. 4, No. 6, pp. 130–136, 1988; Anticancer Research, Vol 6, pp. 543–548, 1986).

Now, the relationship of 3(2H)-pyridazinone derivatives of the general formula (I) and their salts according to the present invention with compounds disclosed in published references will be described.

(a) German Laid Open Patent Application No. 1,670,169 (hereinafter referred to as reference (a)) discloses 3(2H)-pyridazinone derivatives having a hydrogen atom or an aliphatic, cycloaliphatic, araliphatic or aromatic group at the 2-position, a chlorine or bromine atom at the 4-position, an amino group inclusive of an aralkylamino group at the 5-position, and a chlorine or bromine atom or a hydroxy or $C_1-C_4$ alkoxy group at the 6-position.

This reference (a) discloses a process for synthesis of the 3(2H)-pyridazinone derivatives, their application to agricultural chemicals, their application as intermediates for medicines, dyestuffs or various other chemicals, and, however, neither mentions their pharmacological activities nor gives any specific examples of such compounds. Further, such compounds are not specifically described.

(b) Japanese Unexamined Patent Publication No. 183675/1983 (hereinafter referred to as reference (b)) discloses 3(2H)-pyridazinone derivatives having a lower alkyl group at the 2-position, a hydrogen atom at the 4-position, a substituted or unsubstituted anilino group at the 5-position and a hydroxyl group or a lower alkoxy group at the 6-position. This reference (b) discloses that the 3(2H)-pyridazinone derivatives have an analgesic action, an anti-inflammatory action, an anti-allergic action and an anti-rheumatic action, but there is no specific disclosure concerning their pharmacological activities.

(c) Japanese Unexamined Patent Publication No. 301870/1988, European Laid Open Patent Publication No. 275997 and U.S. Pat. No. 4,978,665 (hereinafter referred to collectively as reference (c)) disclose 6-substituted alkoxy-5-substituted benzylamino-3(2H)-pyridazinone derivatives, which are relatively similar to the compounds of the present invention and their use as an anti-SRS-A agent.

(d) International Patent Application WO-91/16314, European Laid Open Patent Publication No. 482208 and U.S. Pat. No. 5,202,323 (hereinafter referred to collectively as reference (d)) disclose 6-substituted alkoxy-5-substituted arylamino-3(2H)-pyridazinone derivatives, which are relatively similar to the compounds of the present invention, and their use as a platelet aggregation inhibitor, a cardiotonic, a vasodilator and an anti-SRS-A agent.

The present invention relates to novel 3(2H)-pyridazinone compounds and their derivatives useful as an antiplatelet agent as an active ingredient of a prophylactic or therapeutic drug for thrombosis and other diseases attributable to pathological activation of the platelet.

DISCLOSURE OF THE INVENTION

As the result of the extensive study, the present inventors have discovered that the 3(2H)-pyridazinone derivatives and their salts of the present invention, which are different from any compounds disclosed in the above references, are very selective and quite useful antiplatelet agents which show an intense and broad spectrum in inhibition of platelet aggregation, hardly act on the heart or the blood vessels and do not produce significant side effects such as headaches, depression, a drop in the blood pressure and palpitations, and that they can be active ingredients of prophylactic or therapeutic drugs for the above-mentioned various thrombotic diseases. On the basis of this discovery, the present invention has been accomplished.

That is, the present invention relates to a 3(2H)-pyridazinone derivative represented by the general formula (I) and its salt, and a pharmaceutical composition containing it as an active ingredient:

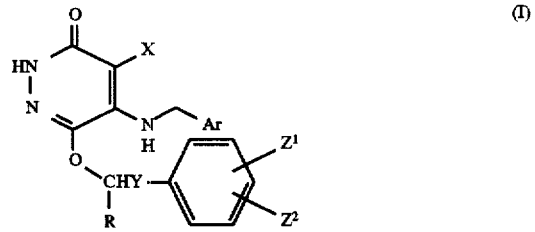

(I)

[wherein R is a hydrogen atom or a $C_1-C_4$ alkyl group,

X is a hydrogen atom, a chlorine atom or a bromine atom,

Ar is a pyridyl group or a phenyl group substituted with $OR^1$ (wherein $R^1$ is a hydrogen atom or a $C_1-C_4$ alkyl group) and A {wherein A is a hydrogen atom, a halogen atom, a $C_1-C_4$ alkyl group or $OR^2$ (wherein $R^2$ is a hydrogen atom or a $C_1-C_4$ alkyl group)}, Y is $C_1-C_8$ alkylene wherein one carbon atom on the straight chain is substituted with one $OR^1$ group (wherein $R^1$ is the same as defined above), and $Z^1$ and $Z^2$ are independently a hydrogen atom, a halogen atom, a $C_1-C_4$ alkyl group or a $OR^1$ group (wherein $R^1$ is the same as defined above)].

Hereinafter, R, $R^1$, $R^2$, X, Y, $Z^1$, $Z^2$ and Ar in the above general formula (I) representing the compound of the present invention are explained.

R, $R^1$ and $R^2$ are respectively a hydrogen atom or a linear or branched $C_1-C_4$ alkyl group. Examples of them include a hydrogen group, a methyl group, an ethyl group, a n-propyl group, an i-propyl group, a n-butyl group, an i-butyl group, a sec-butyl group and a t-butyl group.

As examples of X, a hydrogen atom, a chlorine atom and a bromine atom may be mentioned.

Y is $C_1$-$C_8$ alkylene wherein one carbon on the straight chain is substituted with one $OR^1$ group (wherein $R^1$ is the same as defined above). Examples of Y include hydroxymethylene, methoxymethylene, ethoxymethylene, propoxymethylene, butoxymethylene, 1-hydroxyethylene, 2-hydroxyethylene, 1-methoxyethylene, 2-methoxyethylene, 1-ethoxyethylene, 2-ethoxyethylene, 1-propoxyethylene, 2-propoxyethylene, 1-butoxyethylene, 2-butoxyethylene, 1-hydroxypropylene, 2-hydroxypropylene, 3-hydroxypropylene, 1-methoxypropylene, 2-methoxypropylene, 3-methoxypropylene, 1-ethoxypropylene, 2-ethoxypropylene, 3-ethoxypropylene, 1-propoxypropylene, 2-propoxypropylene, 3-propoxypropylene, 1-butoxypropylene, 2-butoxypropylene, 3-butoxypropylene, 1-hydroxybutylene, 2-hydroxybutylene, 3-hydroxybutylene, 4-hydroxybutylene, 1-methoxybutylene, 2-methoxybutylene, 3-methoxybutylene, 4-methoxybutylene, 1-ethoxybutylene, 2-ethoxybutylene, 3-ethoxybutylene, 4-ethoxybutylene, 1-propoxybutylene, 2-propoxybutylene, 3-propoxybutylene, 4-propoxybutylene, 1-butoxybutylene, 2-butoxybutylene, 3-butoxybutylene, 4-butoxybutylene, 5-hydroxypentylene, 6-hydroxyhexylene, 7-hydroxyheptylene, 8-hydroxyoctylene, 1-hydroxy-1-methylmethylene, 1-hydroxy-2-methylethylene, 2-ethyl-1-hydroxyethylene, 1-hydroxy-2-propylethylene, 2-butyl-1-hydroxyethylene, 1-hydroxy-2-pentylethylene, 2-hexyl-1-hydroxyethylene, 2-hydroxy-1-methylethylene, 1-ethyl-2-hydroxyethylene, 2-hydroxy-1-propylethylene, 1-butyl-2-hydroxyethylene, 2-hydroxy-1-pentylethylene, 1-hexyl-2-hydroxyethylene, 1-hydroxy-2-methylpropylene, 2-ethyl-1-hydroxypropylene, 1-hydroxy-2-propylpropylene, 2-butyl-1-hydroxypropylene, 1-hydroxy-3-methylpropylene, 3-ethyl-1-hydroxypropylene, 1-hydroxy-3-propylpropylene, 3-butyl-1-hydroxypropylene, 1-hydroxy-2-methylbutylene, 2-ethyl-1-hydroxybutylene, 1-hydroxy-2-propylbutylene, 2-butyl-1-hydroxybutylene, 1-hydroxy-3-methylbutylene, 3-ethyl-1-hydroxybutylene, 1-hydroxy-3-propylbutylene, 3-butyl-1-hydroxybutylene, 2,2-dimethyl-1-hydroxyethylene, 2,2-diethyl-1-hydroxyethylene, 2,2-diisopropyl-1-hydroxyethylene, 1,1-dimethyl-2-hydroxyethylene, 1,1-diethyl-2-hydroxyethylene, 1,1-diisopropyl-2-hydroxyethylene, 2,2-dimethyl-1-hydroxypropylene, 2,2-diethyl-1-hydroxypropylene, 1,1-dimethyl-2-hydroxypropylene, 1,1-diethyl-2-hydroxypropylene, 3,3-dimethyl-1-hydroxypropylene, 3,3-diethyl-1-hydroxypropylene, 3,3-dimethyl-2-hydroxypropylene, 3,3-diethyl-2-hydroxypropylene, 1,1-dimethyl-3-hydroxypropylene, 1,1-diethyl-3-hydroxypropylene, 2,2-dimethyl-3-hydroxypropylene, 2,2-diethyl-3-hydroxypropylene, 2,2-dimethyl-1-hydroxybutylene, 2,2-diethyl-1-hydroxybutylene, 1,1-dimethyl-2-hydroxybutylene, 1,1-diethyl-2-hydroxybutylene, 3,3-dimethyl-1-hydroxybutylene, 3,3-diethyl-1-hydroxybutylene, 3,3-dimethyl-2-hydroxybutylene, 3,3-diethyl-2-hydroxybutylene, 1,1-dimethyl-3-hydroxybutylene, 1,1-diethyl-3-hydroxybutylene, 2,2-dimethyl-3-hydroxybutylene and 2,2-diethyl-3-hydroxybutylene.

Examples of $Z^1$ and $Z^2$ include a hydrogen atom, a fluorine atom, a chlorine atom, a bromine atom, an iodine atom, a methyl group, an ethyl group, a n-propyl group, an i-propyl group, a n-butyl group, an i-butyl group, a sec-butyl group, a t-butyl group, a hydroxy group, a methoxy group, an ethoxy group, a n-propoxy group, an i-propoxy group, a n-butoxy group, an i-butoxy group, a sec-butoxy group and a t-butoxy group.

Ar is a pyridyl group or a phenyl group. The phenyl group is substituted with $OR^1$ (wherein $R^1$ is a hydrogen atom or a $C_1$-$C_4$ alkyl group) and with A {wherein A is a hydrogen atom, a fluorine atom, a chlorine atom, a bromine atom, an iodine atom, a $C_1$-$C_4$ alkyl group or $OR^2$ (wherein $R^2$ is a hydrogen atom or a $C_1$-$C_4$ alkyl group)}.

Examples of Ar include pyridyl groups and substituted phenyl groups represented later by Q1–Q33.

However, it should be understood that these specific examples of respective substituents by no means limit the present invention.

In the above description, "n", "i", "sec" and "t" and for "normal", "iso", "secondary" and "tertiary", respectively.

Among the compounds represented by the general formula (I) of the present invention, preferred are: (1) Compounds represented by the general formula (I) of the present invention wherein X is a chlorine atom or a bromine atom.

More preferred are: (2) Compounds (I) of the present invention as defined in (1), wherein Y is $C_1$-$C_8$ alkylene wherein one carbon atom on the straight chain is substituted with one OH group, $Z^1$ is a hydrogen atom, a halogen atom or a $OR^1$ group (wherein $R^1$ is a hydrogen atom or a $C_1$-$C_4$ alkyl group), and $Z^2$ is a hydrogen atom.

Still more preferred are: (3) Compounds (I) of the present invention as defined in (2), wherein Y is $C_1$-$C_4$ alkylene wherein one carbon atom on the straight chain is substituted with one OH group, (4) Compounds (I) of the present invention as defined in (3), wherein A is a hydrogen atom or $OR^2$ (wherein $R^2$ is a hydrogen atom or a $C_1$-$C_4$ alkyl group), and (5) Compounds (I) of the present invention as defined in (4), wherein $Z^1$ is a fluorine atom, a chlorine atom or a bromine atom.

Having from 1 to 6 asymmetric carbon atoms, the compounds of the general formula (I) of the present invention include optical isomers and stereoisomers.

Hereinafter, typical compounds representing the 3(2H)-pyridazinone derivatives and their salts of the present invention are illustrated in the following Table I, but the present invention should not be limited thereto.

In Table I, "n", "i", "sec", "Me", "Et", "Pr", "Bu" and "Ph" stand for normal, iso, secondary, a methyl group, an ethyl group, a propyl group, a butyl group and a phenyl group, respectively.

Q1–Q33 in Table I are groups represented by the following formulas.

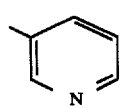
Q1

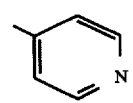
Q2

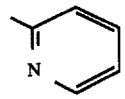
Q3

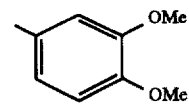
Q4

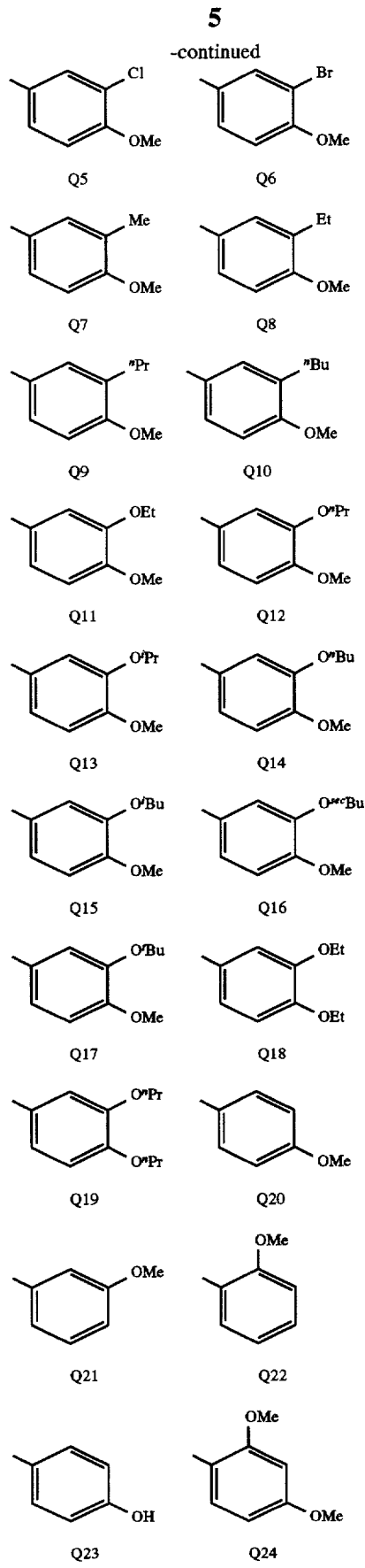

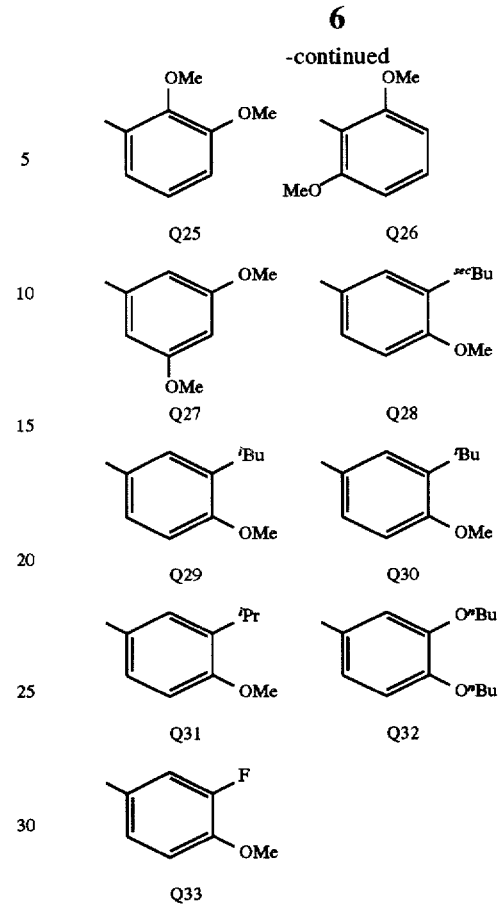

| No. | X | Ar | R | Y | $Z^1$ | $Z^2$ |
|---|---|---|---|---|---|---|
| 1 | Br | Q1 | H | $CH_2CH(OH)$ | 4-Cl | H |
| 2 | Br | Q4 | H | $CH_2CH(OH)$ | 4-Cl | H |
| 3 | Br | Q2 | H | $CH_2CH(OH)$ | 4-Cl | H |
| 4 | Br | Q3 | H | $CH_2CH(OH)$ | 4-Cl | H |
| 5 | Br | Q5 | H | $CH_2CH(OH)$ | 4-Br | H |
| 6 | Br | Q6 | H | $CH_2CH(OH)$ | H | H |
| 7 | Br | Q7 | H | $CH_2CH(OH)$ | H | H |
| 8 | Br | Q8 | H | $CH_2CH(OH)$ | H | H |
| 9 | Br | Q9 | H | $CH_2CH(OH)$ | H | H |
| 10 | Br | Q10 | H | $CH_2CH(OH)$ | H | H |
| 11 | Br | Q11 | H | $CH_2CH(OH)$ | H | H |
| 12 | Br | Q12 | H | $CH_2CH(OH)$ | H | H |
| 13 | Br | Q13 | H | $CH_2CH(OH)$ | H | H |
| 14 | Br | Q14 | H | $CH_2CH(OH)$ | H | H |
| 15 | Br | Q15 | H | $CH_2CH(OH)$ | H | H |
| 16 | Br | Q16 | H | $CH_2CH(OH)$ | H | H |
| 17 | Br | Q17 | H | $CH_2CH(OH)$ | H | H |
| 18 | Br | Q18 | H | $CH_2CH(OH)$ | H | H |
| 19 | Br | Q19 | H | $CH_2CH(OH)$ | H | H |
| 20 | Br | Q20 | H | $CH_2CH(OH)$ | H | H |
| 21 | H | Q1 | H | $CH_2CH(OH)$ | H | H |
| 22 | Cl | Q1 | H | $CH_2CH(OH)$ | H | H |
| 23 | Cl | Q1 | H | $CH_2CH(OH)$ | 3-Me | 4-Me |
| 24 | Cl | Q1 | H | $CH_2CH(OH)$ | 4-Et | H |

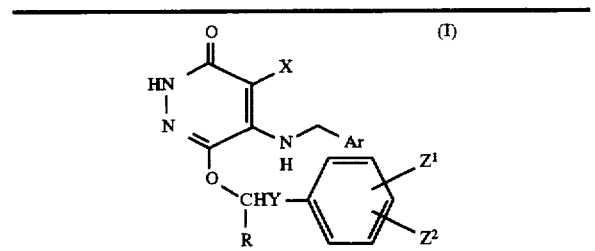

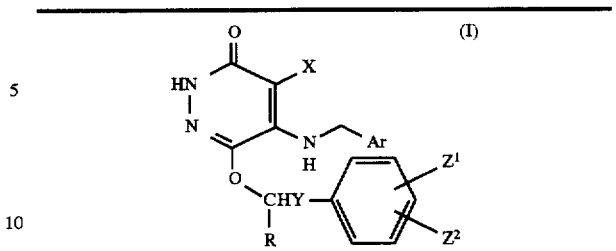

| No. | X | Ar | R | Y | $Z^1$ | $Z^2$ |
|---|---|---|---|---|---|---|
| 25 | Cl | Q1 | H | CH$_2$CH(OH) | 4-$^n$Pr | H |
| 26 | Cl | Q1 | H | CH$_2$CH(OH) | 4-$^i$Pr | H |
| 27 | Cl | Q1 | H | CH$_2$CH(OH) | 4-$^n$Bu | H |
| 28 | Cl | Q1 | H | CH$_2$CH(OH) | 4-$^i$Bu | H |
| 29 | Cl | Q1 | H | CH$_2$CH(OH) | 4-$^{sec}$Bu | H |
| 30 | Cl | Q1 | H | CH$_2$CH(OH) | 4-$^t$Bu | H |
| 31 | Br | Q1 | H | CH$_2$CH(OH) | 3-OMe | 4-OMe |
| 32 | Br | Q1 | H | CH$_2$CH(OH) | 4-OEt | H |
| 33 | Br | Q1 | H | CH$_2$CH(OH) | 4-O$^n$Pr | H |
| 34 | Br | Q1 | H | CH$_2$CH(OH) | 4-O$^i$Pr | H |
| 35 | Br | Q1 | H | CH$_2$CH(OH) | 4-O$^n$Bu | H |
| 36 | Br | Q1 | H | CH$_2$CH(OH) | 4-O$^i$Bu | H |
| 37 | Br | Q1 | H | CH$_2$CH(OH) | 4-O$^{sec}$Bu | H |
| 38 | Br | Q1 | H | CH$_2$CH(OH) | 4-O$^t$Bu | H |
| 39 | Br | Q1 | H | CH$_2$CH(OH) | 2-O$^i$Pr | 4-OMe |
| 40 | Br | Q1 | H | CH$_2$CH(OH) | 3-Cl | 4-Cl |
| 41 | Br | Q1 | Me | (CH$_2$)$_2$CH(OH) | H | H |
| 42 | Br | Q4 | H | (CH$_2$)$_3$CH(OH) | H | H |
| 43 | Br | Q4 | H | (CH$_2$)$_4$CH(OH) | H | H |
| 44 | Br | Q4 | H | (CH$_2$)$_5$CH(OH) | H | H |
| 45 | Br | Q4 | H | CH(OH)CH$_2$ | H | H |
| 46 | Br | Q4 | H | CH(OH)(CH$_2$)$_2$ | H | H |
| 47 | Br | Q4 | H | CH(OH)(CH$_2$)$_3$ | H | H |
| 48 | Br | Q4 | H | CH(OH)(CH$_2$)$_4$ | H | H |
| 49 | Br | Q4 | H | CH(OH)(CH$_2$)$_5$ | H | H |
| 50 | Br | Q4 | H | CH$_2$CH(OH)CH$_2$ | 4-Cl | H |
| 51 | Br | Q4 | H | (CH$_2$)$_2$CH(OH)CH$_2$ | 4-Cl | H |
| 52 | Br | Q4 | H | (CH$_2$)$_2$CH(OH)(CH$_2$)$_2$ | 4-Cl | H |
| 53 | Br | Q4 | H | CH(Me)CH(OH) | 4-Cl | H |
| 54 | Br | Q4 | H | CH(OH)C(Me)$_2$ | 4-Cl | H |
| 55 | Br | Q1 | H | CH$_2$CH(OMe) | 4-Cl | H |
| 56 | Br | Q1 | H | CH$_2$CH(OMe)CH$_2$ | 4-Cl | H |
| 57 | Br | Q4 | H | CH(OMe)CH$_2$ | 4-Cl | H |
| 58 | Br | Q4 | H | CH$_2$CH(OEt) | 4-Cl | H |
| 59 | Br | Q4 | H | CH$_2$CH(O$^n$Pr) | 4-Cl | H |
| 60 | Br | Q4 | H | CH$_2$CH(O$^n$Bu) | 4-Cl | H |
| 61 | H | Q4 | H | CH$_2$CH(OH) | 4-Cl | H |
| 62 | Br | Q4 | Et | CH$_2$CH(OH) | 4-Cl | H |
| 63 | Br | Q4 | $^n$Pr | CH$_2$CH(OH) | 4-Cl | H |
| 64 | Br | Q4 | H | CH$_2$CMe(OH)CH$_2$ | 4-Cl | H |
| 65 | Br | Q1.HCl | H | CH$_2$CH(OH) | 4-Cl | H |
| 66 | Br | Q21 | H | CH$_2$CH(OH) | 4-Cl | H |
| 67 | Br | Q22 | H | CH$_2$CH(OH) | 4-Ci | H |
| 68 | Br | Q23 | H | CH$_2$CH(OH) | 4-Cl | H |
| 69 | Br | Q24 | H | CH$_2$CH(OH) | 4-Cl | H |
| 70 | Br | Q25 | H | CH$_2$CH(OH) | 4-Cl | H |
| 71 | Br | Q26 | H | CH$_2$CH(OH) | 4-Cl | H |
| 72 | Br | Q27 | H | CH$_2$CH(OH) | 4-Cl | H |
| 73 | Br | Q28 | H | CH$_2$CH(OH) | 4-Cl | H |
| 74 | Br | Q29 | H | CH$_2$CH(OH) | 4-Cl | H |
| 75 | Br | Q30 | H | CH$_2$CH(OH) | 4-Cl | H |
| 76 | H | Q31 | H | CH$_2$CH(OH) | 4-Cl | H |
| 77 | Br | Q1 | H | C(Et)$_2$CH(OH) | 4-Cl | H |
| 78 | Br | Q1 | H | C($^i$Pr)$_2$CH(OH) | 4-Cl | H |
| 79 | Br | Q32 | H | CH$_2$CH(OH) | 4-Cl | H |
| 80 | Br | Q1 | $^n$Bu | CH$_2$CH(OH) | 4-Cl | H |
| 81 | Br | Q1 | H | CH(OH) | 4-Cl | H |
| 82 | Br | Q1 | H | CH$_2$CH(OH) | OH | H |
| 83 | Cl | Q1 | H | *R CH$_2$CH(OH) | 4-Cl | H |
| 84 | Cl | Q4 | H | *R CH$_2$CH(OH) | 4-Cl | H |
| 85 | Br | Q1 | H | *R CH$_2$CH(OH) | 4-Cl | H |
| 86 | Br | Q4 | H | *R CH$_2$CH(OH) | 4-Cl | H |
| 87 | Cl | Q1 | H | *R CH$_2$CH(OH) | 4-Cl | H |
| 88 | Br | Q4 | H | *R CH$_2$CH(OH) | 4-Cl | H |
| 89 | Cl | Q1 | H | *S CH$_2$CH(OH) | 4-Cl | H |
| 90 | Br | Q4 | H | *S CH$_2$CH(OH) | 4-Cl | H |
| 91 | Br | Q1 | H | *S CH$_2$CH(OH) | 4-Cl | H |
| 92 | Br | Q1.HCl | H | *S CH$_2$CH(OH) | 4-Cl | H |
| 93 | Br | Q1.HCl | H | *R CH$_2$CH(OH) | 4-Cl | H |
| 94 | Br | Q1 | H | CH(OH)CH$_2$ | 4-Cl | H |
| 95 | Br | Q1 | H | *S CH(OH)CH$_2$ | 4-Cl | H |
| 96 | Br | Q1 | H | *R CH(OH)CH$_2$ | 4-Cl | H |

Methods for preparing the compounds of the present invention are explained hereinafter.

The 3(2H)-pyridazinone derivatives of the general formula (I) and their salts of the present invention can be prepared by the following methods as illustrated by the reaction formulas (1)–(2).

Reaction formula (1)

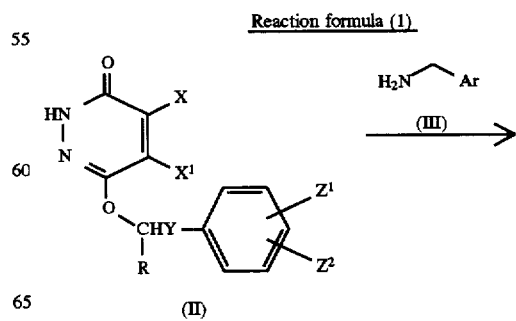

-continued

Reaction formula (1)

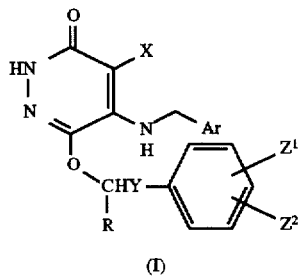

(I)

(wherein $X^1$ is a chlorine atom or a bromine atom, and R, X, Y, $Z^1$, $Z^2$ and Ar are the same as defined above.)

In the preparation method according to the reaction formula (1), a 5-halo 3-(2H)-pyridazinone compound of the general formula (II) is reacted with an arylmethylamine derivative of the general formula (III) or its salt optiionally in the presence of a dehydrohalogenating agent in an inert solvent to produce a compound of the general formula (I).

In this reaction, any inert solvents may be used. For example, an ether type solvent (such as tetrahydrofuran or 1,4-dioxane), an amide type solvent (such as formamide, N,N-dimethylformamide or N-methylpyrrolidone), acetonitrile, dimethyl sulfoxide, an alcohol type solvent (such as methanol, ethanol or propanol), an organic amine type solvent (such as pyridine, triethylamine, N,N-dimethylaminoethanol or triethanolamine), water, a hydrocarbon type solvent (such as benzene, toluene, xylene, n-hexane or n-heptane) or a solvent mixture thereof, may be mentioned. Particularly preferred are polar solvents such as an ether type solvent, an amide type solvent, acetonitrile, dimethyl sulfoxide, an alcohol type solvent, an organic amine type solvent, water and solvent mixtures thereof.

Any dehydrohalogenating agents may be used so long as they do not adversely affect the reaction and are capable of trapping a hydrogen halide. As such a dehydrohalogenating agent, an inorganic base such as potassium carbonate, sodium carbonate, potassium hydrogen carbonate or sodium hydrogen carbonate, or an organic base such as N,N-dimethylaniline, N,N-diethylaniline, trimethylamine, triethylamine, N,N-dimethylaminoethanol or pyridine, may be mentioned.

Otherwise, the starting material, an arylmethylamine derivative of the general formula (III), may be used in an excessive amount as the dehydrohalogenating agent.

The reaction temperature may be within a range of from 10° C. to the boiling point of the solvent used for the reaction.

The molar ratio of the starting materials may optionally be set. However, the arylmethylamine derivative of the general formula (III) or its salt may be used usually in an amount of from 1 to 10 mols, preferably from 1.2 to 5 mols, relative to one mol of the 5-halo-3(2H)-pyridazinone derivative of the general formula (II).

The 5-halo-3(2H)-pyridazinone derivative of the general formula (II) can be prepared by the conventional process or by application of the conventional organic reaction as described below.

Namely, the 5-halo-3(2H)-pyridazinone derivative of the general formula (II) can be prepared by the methods disclosed in the above-mentioned references (c) and (d).

Among the arylmethylamine derivatives of the general formula (III) and their salts in the reaction formula (1), those not available as commercial products can be prepared by the methods disclosed in Japanese Unexamined Patent Publication No. 267560/1986, European Patent No. 186817 and U.S. Pat. No. 5,098,900.

The compound of the formula (I) thus prepared can readily be purified by conventional methods known per se in organic synthesis, such as fractional recrystallization and various silica gel chromatography.

Reaction formula (2)

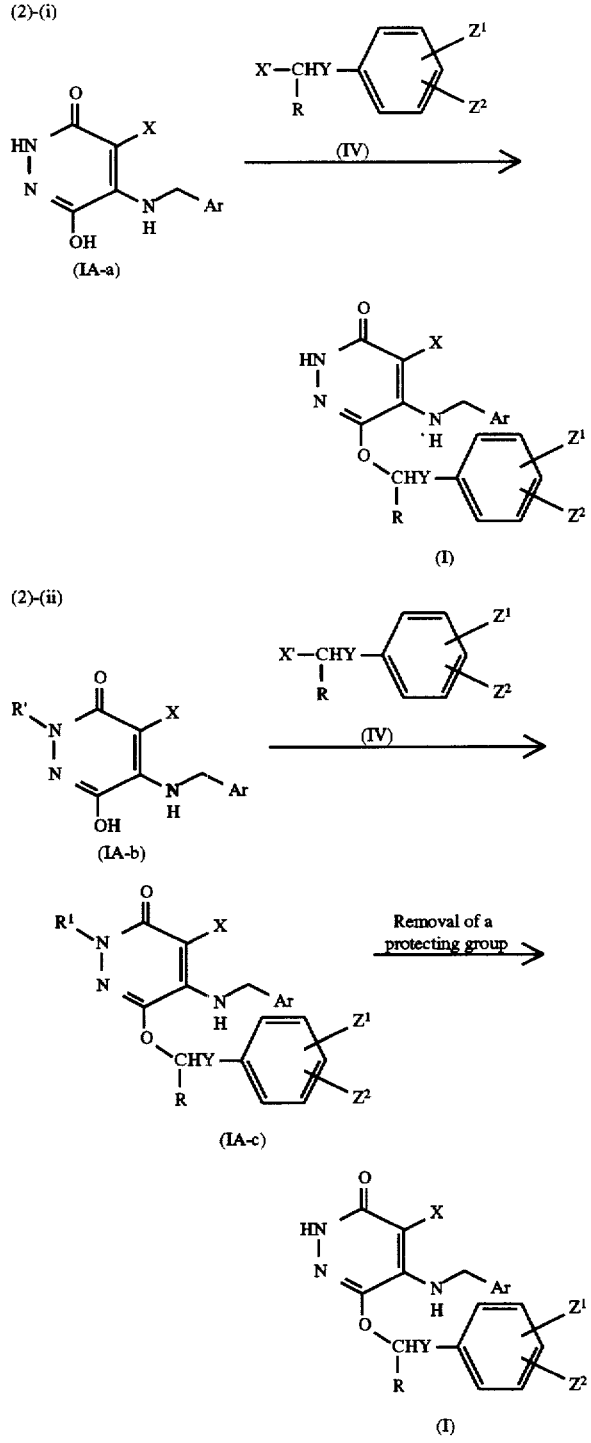

(wherein X' is an eliminable functional group such as a p-toluenesulfonyloxy group, a methanesulfonyloxy group, a chlorine atom, a bromine atom or an iodine atom, R' is a protecting group, and R, X, Y, $Z^1$, $Z^2$ and Ar are the same as defined above.)

The above reaction formula (2) illustrates a method for preparing a compound of the general formula (I) of the present invention by reacting a 6-hydroxy-5-arylmethylamino derivative of the general formula (IA-a) or (IA-b) with a reactive derivative of the formula (IV).

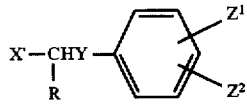 (IV)

The 6-hydroxy-5-arylmethyl derivative of the formula (IA-a) used as the starting material in the present reaction can be prepared in accordance with the method disclosed in the above-mentioned reference (c).

The compound (I) can be synthesized by this reaction either via the direct route as shown in the reaction formula (2)-(i) from the starting material having hydrogen at the 2-positon, or via the route as shown in the reaction formula (2)-(ii) from the 6-hydroxy-5-arylmethylamino derivative of the general formula (IA-b) protected at the 2-position with R', by converting it into a compound of the general formula (IA-c) and then removing the protecting group R'.

As the protecting group R', tetrahydropyranyl, tetrahydrofuranyl, 2-trimethylsilylethoxymethyl ($Me_3SiCH_2CH_2OCH_2$—), pivaloyloxymethyl ($Me_3CCO_2CH_2$—), benzyloxymethyl ($PhCH_2OCH_2$—), hydroxymethyl, methoxymethyl ($MeOCH_2$—) or $CO_2R''$ (wherein R" is a lower alkyl group), is preferably used.

The removal of the protecting group R' can easily be conducted by a conventional method for the removal of such protecting groups.

The present reaction can be generally conducted in the presence of an inorganic base such as potassium carbonate, sodium carbonate, lithium carbonate, potassium hydrogen carbonate, sodium hydrogen carbonate, lithium hydroxide, etc., or an organic base such as triethylamine, tri-n-propylamine, etc.

As a reaction solvent, a ketone type solvent (acetone, methyl ethyl ketone, diethyl ketone, etc.), an amide type solvent (formamide, N,N-dimethylformamide, N,N-diethylacetamide, etc.), an alcohol type solvent (methanol, ethanol, etc.), water and a mixture thereof can be suitably used.

The reaction temperature is usually within a range of from 0° C. to the boiling point of the solvent. The molar ratio of the starting materials may optionally be determined. However, it is sufficient that the reactive derivative of the general formula (IV) is used in an amount of from 1 to 5 mols relative to one mol of the compound of the general formula (IA-a) or (IA-b).

The desired compound can be isolated and purified in accordance with the method as described with respect to the reaction formula (1).

An optically active 3(2H)-pyridazinone derivative of the general formula (I) can be obtained by conventional optical resolution of a racemic 3(2H)-pyridazinone derivative (I) as the final product in the reaction formula (1) or (2), or by using an optically active intermediate (II), (IV) or (IA-c) in these reactions.

As the manner of administration of the 3(2H)-pyridazinone derivatives of the general formula (I) or their pharmaceutically acceptable salts of the present invention, there may be mentioned parenteral administration in the form of injections (for subcutaneous, intravenous, intramuscular or intraperitoneal injection), ointments, suppositories or aerosols, or oral administration in the form of tablets, capsules, granules, pills, syrups, liquids, emulsions or suspension.

The above pharmacological composition contains a compound of the present invention in an amount of from about 0.1 to about 99.5% by weight, preferably from about 0.5 to 95% by weight, based on the total weight of the composition.

To the compound of the present invention or to the composition containing the compound of the present invention, other pharmacologically active compounds may be incorporated.

Further, the composition of the present invention may contain a plurality of compounds of the present invention.

The clinical dose of the compound of the present invention varies depending upon the age, the body weight, the sensitivity or the condition, etc. of the patient. However, the effective daily dose is usually from 0.003 to 1.5 g, preferably from 0.01 to 0.6 g, for an adult.

However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as syrups, gum arabic, gelatin, sorbitol, tragacanth, methyl cellulose or polyvinyl pyrrolidone; a disintegrant such as starch, carboxymethyl cellulose or its calcium salt, crystalline cellulose or polyethylene glycol; a gloss agent such as talc, magnesium or calcium stearate or silica; or a lubricant such as sodium laurate or glycerol.

The injections, syrups, solutions, emulsions, suspensions or aerosols, may be prepared by using a solvent for the active ingredient such as water, ethyl alcohol, isopropyl alcohol, propylene glycol, 1,3-butylene glycol, or polyethylene glycol; a surfactant such as a sorbitan fatty acid ester, a polyoxyethylene fatty acid ester, a polyoxyethylene ether of hydrogenated castor oil or lecithin; a suspending agent such as a cellulose derivative such as methyl cellulose or sodium carboxymethyl cellulose, or a natural rubber such as tragacanth or gum arabic; or a preservative such as a p-hydroxybenzoate ester, benzalkonium chloride or a salt of sorbic acid.

Likewise, the suppositories may be prepared by using e.g. polyethylene glycol, lanolin or coconut oil.

BEST MODE FOR CARRYING OUT THE INVENTION

Now, the present invention will be described in detail with reference to Examples (including Preparation Examples, Formulation Examples and Test Examples). However, it should be understood that the present invention is by no means restricted by these specific Examples.

In Preparation Examples, the symbol "MS" indicates "mass spectrum".

PREPARATION EXAMPLES

Reference Example 1

1-(4-chorophenyl)-1,3-propanediol

To a solution of 5.0 g of ethyl-4-chlorobenzoylacetate in 100 ml of methylene chloride cooled to −30° C., 77.3 ml of diisopropylaluminium hydride (1.0 mol/l toluene solution) was added, and the resulting mixture was stirred for 30 minutes and then brought back to room temperature over 3 hours, and 4.14 g of methanol and 24.3 g of water were added carefully, and the mixture was stirred for another 1.5 hours. The precipitate was filtered off, and the filtrate was concentrated. The resulting residue was purified by silica gel column chromatography (eluent; n-hexane/ethyl acetate=1/1), to obtain 2.45 g of the title compound as a pale yellow oily substance.

Reference Example 2

3-(4-chlorophenyl)-3-hydroxypropyl-1-tosylate

To a liquid mixture of 2.30 g of 1-(4-chlorophenyl)-1,3-propanediol and 20 ml of pyridine cooled to -20° C., a liquid mixture of 2.58 g of p-toluenesulfonyl chloride and 5 ml of pyridine was added. The resulting mixture was stirred at 0° C. for 4 hours, then brought back to room temperature and then stirred for another 1 hour. It was cooled again to -20° C., and dilute hydrochloric acid was added until a white precipitate was formed. Then, it was extracted with ethyl acetate. The extract was washed with a saturated saline solution and dried over sodium sulfate, and the solvent was distilled off. The resulting residue was purified by silica gel column chromatography (eluent; n-hexane/ethyl acetate=3/1) to obtain 3.31 g of the title compound as a pale yellow oily substance.

Reference Example 3

4,5-dibromo-6-[3-(4-chloropenyl)-3-hydropropyloxy]- 3(2H)pyridazinone

A liquid mixture of 3.86 g of 4,5-dibromo-3,6-dihydroxypyridazine, 3.25 g of 3-(4-chorophenyl)-3-hydroxypropyl-1-tosylate, 1.25 g of triethylamine and 50 ml of N,N-dimethylformamide was stirred at 60° C. for 12 hours. The solvent was distilled off under reduce pressure, then water was poured upon the residue, and the residue was dissolved by heating to 100° C. and then allowed to cool. The precipitated crystals were filtered out and dried under reduced pressure. The crystals thus obtained were recrystallized from methanol-water and washed with methanol to obtain 1.55 g of the title compound as white crystals having a melting point of 232°–239° C.

MS (m/e): 436(M+), 420, 359, 271, 141 (100%), 133, 77.

Reference Example 4

(2S,3R)-3-(4-chlorophenyl)-2,3-epoxy-1-propanol

To 520 ml of a methylene chloride solution of 10.98 g of titanium tetraisopropoxide cooled to -70° C., 12 ml of a methylene chloride solution of 12.07 g of D-(-)-diethyl tartarate was added dropwise, and the resulting mixture was stirred for 20 minutes. Then, 25 ml of a methylene chloride solution of 12.9 g of p-chlorocinnamyl alcohol was added dropwise, and the resulting mixture was stirred for 20 minutes. Then, 42.0 ml of t-butyl hydroperoxide (3.67 mol/l methylene chloride solution) was added dropwise, and the resulting mixture was stirred at 70° C. for 1.5 hours, at -40° C. for 2 hours and at -20° C. for 1.5 hours, and then brought to -10° C. over 1 hour and stirred at the same temperature for 2 hours. After it was cooled again to -20° C., 150 ml of an aqueous solution of 38.5 g of iron sulfate hexahydrate and 15.4 g of citric acid monohydrate was added dropwise over 0.5 hour below 5° C. The mixture was stirred vigorously at 0° C. for 0.5 hour and filtered through celite. The filtrate was allowed to separate, and the aqueous layer was extracted again with methylene chloride. The organic layers were combined and washed with a saturated sodium hydrogen carbonate aqueous solution, water and a saturated saline solution. After the solvent was distilled off, the residue was dissolved in diethyl ether, and sodium sulfate and activated carbon were added, and the mixture was allowed to stand for 0.5 hour. The mixture was filtered through celite, and the ether solution thus obtained was cooled with ice. 172 ml of 1N sodium hydroxide aqueous solution was added, and then, the resulting mixture was stirred vigorously for 1 hour. After it was allowed to separate, the organic layer was washed with water (twice) and with a saturated saline solution, treated with activated carbon and filtered through celite. After the solvent was distilled off, the residue was purified by silica gel chromatography (eluent; methanol/chloroform= 1/99) and crystallized from cyclohexane to obtain 6.35 g of the title compound as white crystals of $[\alpha]_D^{25}+39.42°$ (chloroform, c 1.042).

Reference Example 5

(1S)-1-(4-chlorophenyl)-1,3-propanediol 500 ml of a dimethoxyethane solution of 15.0 g of (2S,3R)-3-(4-chlorophenyl)-2,3-epoxy-1-propanol was cooled to -25° C., and 25.1 ml of a red-Al solution (3.4 mol/l toluene solution) was added dropwise over 0.5 hour. After stirred at 20° C. for 2 hours, the mixture was brought to 0° C. over 1 hour, and 300 ml of diethyl ether was added thereto. While the mixture was kept below 5° C., 100 ml of 2N hydrochloric acid was added dropwise. After stirring for 15 minutes, the mixture was filtered through celite. Then, 100 ml of ethyl acetate was added, and the resulting mixture was allowed to separate. The aqueous layer was extracted again with ethyl acetate. The organic layers were combined, dried over sodium sulfate and filtered through celite. The solvent was distilled off the filtrate, and the resulting residue was purified by silica gel column chromatography (eluent; methanol/chloroform=5/95). It was crystallized to obtain 14.56 g of the title compound as white crystals.

Reference Example 6

(3S)-3-(4-chorophenyl)-3-hydroxypropyl-1-tosylate

To a liquid mixture of 14 g of (1S)-1-(4-chlorophenyl)-1,3-propanediol with 126 ml of pyridine cooled to -30° C., a liquid mixture of 18.5 g of p-toluenesulfonyl chloride with 37 ml of pyridine was added dropwise, and the resulting mixture was stirred at room temperature for 3 hours. It was cooled again to -30° C., and after addition of 336 ml of 6N hydrochloric acid, it was brought to room temperature and extracted with ethyl acetate. The extract was washed with a saturated saline solution and dried over sodium sulfate, and the solvent was distilled off. The resulting residue was purified by silica gel chromatography (eluent; n-hexane/ ethyl acetate=2/1) to obtain 22.8 g of the title compound as a pale yellow oily substance.

Reference Example 7

4,5-dibromo-6-[(3S)-3-(4-chlorophenyl)-3-hydroxypropyloxy]-3(2H)pyridazinone

A liquid mixture of 27.1 g of 4,5-dibromo-3,6-dihydroxypyridazine, 22.8 g of (3S)-3-(4-chlorophenyl)-3-hydroxypropyl-1-tosylate, 8.8 g of triethylamine and 280 ml of N,N-dimethylformamide was stirred at 70° C. for 5 hours. The solvent was distilled off under reduced pressure, and to the residue, 100 ml of ethyl acetate, 100 ml of a saturated aqueous sodium hydrogen carbonate solution and 100 ml of water were added. The resulting mixture was stirred at room temperature for 1 hour and then under cooling with ice for 1 hour. The precipitated crystals were filtered out and dried under reduced pressure to obtain 14.65 g of the title compound as white crystals.

Example 1

4-bromo-6-[3-(4-chlorophenyl)-3-hydroxypropyloxy]-5-(3- pyridylylmethylamino)-3 (2H)pyridazinone (Compound No. 1)

A mixture of 1.50 g of 4,5-dibromo-6-[3-(4-chlorophenyl)-3-hydroxylpropyloxy]-3(2H)pyridazinone, 1.48 g of 3-picolylamine, 45 ml of methanol and 5 ml of water was refluxed under heating and stirring overnight. The mixture was cooled with ice, and the precipitated crystals were filtered out and dried under reduced pressure. The resulting crude crystals were recrystallized from methanol to obtain 1.05 g of the title compound as white crystals having a melting point of 212°–214° C.

MS (m/e): 464 (M+), 446, 385, 297, 217, 139, 111, 92 (100%), 77.

Example 2

4-bromo-6-[3-(4-chlorophenyl)-3-hydroxypropyloxy]-5-(3- pyridylylmethylamino)-3 (2H)pyridazinone hydrochloride (Compound No. 65)

A mixture of 1.0 g of 4-bromo-6-[3-(4-chlorophenyl)-3-hydroxypropyloxy]-5-(3-pyridylylmethylamino)- 3(2H) pyridazinone, 3 ml of 1N hydrochloric acid, 12 ml of water and 5 ml of ethanol was stirred at 50° C. for 30 minutes and then cooled with ice. The precipitated crystals were filtered out and dried under reduced pressure to obtain 856 mg of the title compound as white crystals having a melting point of 206°–212° C.

MS (m/e): 464 (M+HCl), 446, 385, 367, 297, 217, 141 (100%), 111, 91, 77.

Example 3

4-bromo-6-[3-(4-chlorophenyl)-3-hydroxypropyloxy]-5-(3,4- dimethoxybenzylamino)-3(2H)pyridazinone (Compound No. 2)

From 300 mg of 4,5-dibromo-6-[3-(4-chlorophenyl)-3-hydroxypropyloxy]-3(2H)pyridazinone, 228 mg of 3,4-dimethoxybenzylamine and 69 mg of triethylamine, 246 mg of the title compound was prepared in the same manner as in Example 1, as white crystals having a melting point of 190°–196° C.

MS (m/e): 523 (M+), 446, 277, 196, 151 (100%)

Example 4

4-bromo-6-[(3S)-3-(4-chlorophenyl)-3-hydroxypropyloxy]-5- (3-pyridylylmethylamino)-3 (2H)pyridazinone (Compound No. 91)

A mixture of 10.0 g of 4,5-dibromo-6-[(3S)-3-(4-chlorophenyl)-3-hydroxypropyloxy]-3(2H)pyridazinone, 9.9 g of 3-picolylamine, 40 ml of methanol and 4 ml of water was refluxed under heating and stirring overnight and then cooled with ice. The precipitated crystals were filtered out and dried under reduced pressure. The resulting crude crystals were recrystallized from a liquid mixture of N,N-dimethylformamide and ethyl acetate to obtain 6.28 g of the title compound as white crystals having a melting point of 200.5°–201.3° C.

MS (FAB; m/e): 465 (M+1)

Example 5

4-bromo-6-[(3S)-3-(4-chlorophenyl)-3-hydroxylpropyloxy]- 5-(3-pyridylylmethylamino)-3 (2H)pyridazinone hydrochloride (Compound No. 92)

500 mg of 4-bromo-6-[(3S)-3-(4-chlorophenyl)-3-hydroxylpropyloxy]-5-(3-pyridylylmethylamino)-3(2H) pyridazinone was dissolved in 5 ml of 10% solution of HCl in ethanol, and the solvent was distilled off. The residue was crystallized from methanol and diethyl ether. The precipitated crystals were filtered out and dried under reduced pressure to obtain 433 mg of the title compound as white crystals having a melting point of 176°–181° C.

Example 6

4-bromo-6-[(3R)-3-(4-chlorophenyl)-3-hydroxylpropyloxy]- 5-(3-pyridylylmethylamino)-3 (2H)pyridazinone hydrochloride (Compound No. 93)

By using (1R)-1-(4-chlorophenyl)-1,3-propanediol as a starting material, the title compound was synthesized in the same manner as 4-bromo-6-[(3S)-3-(4-chlorophenyl)-3-hydroxypropyloxy]-5-(3-pyridylylmethylamino)-3(2H) pyridazinone.

FORMULATION EXAMPLES

Formulation Example 1

| Tablets | |
| --- | --- |
| Compound No. 1 | 10 g |
| Lactose | 20 g |
| Starch | 4 g |
| Starch for paste | 1 g |
| Magnesium stearate | 0.1 g |
| Calcium carboxymethylcellulose | 7 g |
| Total | 42.1 g |

The above components were mixed in a usual manner, and formulated into sugar-coated tablets each containing 50 mg of an active ingredient.

Formulation Example 2

| Capsules | |
| --- | --- |
| Compound No. 3 | 10 g |
| Lactose | 20 g |
| Crystalline cellulose | 10 g |
| Magnesium stearate | 1 g |
| Total | 41 g |

The above components were mixed in a usual manner, and filled into gelatin capsules to obtain capsules each containing 50 mg of an active ingredient.

17
TEST EXAMPLE

Antiplatelet Aggregation Effect

Test Method

Blood was collected from the abdominal aortae of male Wister rats (weight: 200 to 300 g) or male Japanese white rabbits (weight: 1.8 to 2.5 kg) into a syringe containing 1/10 volume 3.8% sodium citrate. The blood thus obtained was centrifuged at 200×g for 7 minutes at room temperature to obtain platelet rich plasma (PRP). Furthermore, the residue was centrifuged at 2000×g for 10 minutes to obtain platelet poor plasma (PPP). The measurement was effected by diluting PRP and PPP to 300,000/mm$^3$. PRP and PPP were put in cuvettes, and the measurement range of transmittance was adjusted to 0% in the case of PRP and to 100% in the case of PPP. Thereafter, a test sample drug dissolved in 100% dimethyl sulfoxide (DMSO) was added to PRP (the final concentration of DMSO: 0.25%). After incubation at 37° C. and 900 rpm for 2 minutes, an aggregating agent was added to measure an aggregation curve. The antiplatelet aggregation effect of the test sample drug was expressed by a concentration, $IC_{50}$ (μM), at which the aggregation of control sample was 50% inhibited. The aggregating agents ADP and collagen were used at minimum concentrations (ADP: 5 to 10 μM; collagen : 2.5 to 10 μg/ml) which caused maximum aggregation. The measurement of platelet aggregation was carried out by using NBS HEMA TRACER 601.

Test Results

Tables II and III show antiplatelet aggregation effects of test compounds evaluated as $IC_{50}$ values (μM).

As a comparative compound, the following compound disclosed in reference (d) was used.

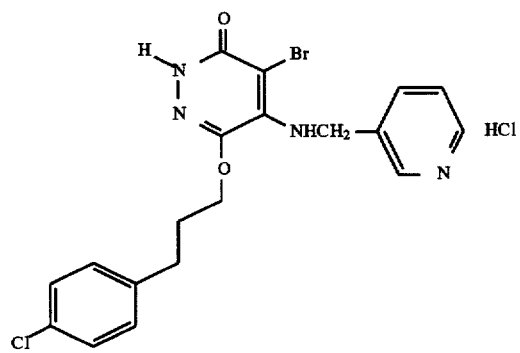

TABLE II

| Test Compound No. | Rat PRP ADP | $IC_{50}$ (μM) Collagen |
|---|---|---|
| 1 | 0.23 | 0.099 |
| 2 | 0.072 | 0.19 |
| 65 | 0.21 | 0.22 |

TABLE III

| Test Compound No. | Rabbit PRP ADP | $IC_{50}$ (μM) Collagen |
|---|---|---|
| 1 | 0.050 | 0.010 |
| 2 | 0.041 | 0.02 |
| 65 | 0.053 | 0.019 |

18

TABLE III-continued

| Test Compound No. | Rabbit PRP ADP | $IC_{50}$ (μM) Collagen |
|---|---|---|
| 93 | 0.047 | 0.0097 |
| Comparative Compound | 0.081 | 0.017 |
| Cilostazol | 15 | 2.4 |

The results demonstrate that the compounds of the present invention have antiplatelet aggregation effects comparable to or higher than that of the comparative compound.

TEST EXAMPLE 2

Vasodilation Effect

Test Method

By using a rabbit thoracic aorta ring specimen, the relaxation effect of a test sample drug on contraction by phenylephrine ($10^{-5}$M) was evaluated. A test sample drug was administered cumulatively from a concentration of $3\times10^{-9}$M, after the contraction became stable. The results were expressed on the basis that the relaxation effect of papaverine hydrochloride ($10^{-4}$M) was 100%.

Test Results

Table IV shows vasodilation effects of test compounds evaluated as $EC_{50}$ values (μM). The comparative compound was the same as in Test Example 1.

TABLE IV

| Test Compound No. | $EC_{50}$ (μM) |
|---|---|
| 1 | 1.3 |
| Comparative Compound | 0.4 |

These results demonstrate that the compound of the present invention has a still weaker vasodilation effect than the comparative compound and, as an antiplatelet agent, has weak side effect.

INDUSTRIAL APPLICABILITY

As evident from the above results, it is clear that the compound of the present invention show an extensive and broad spectrum in inhibition of platelet aggregation and can be an excellent antiplatelet agent which acts very selectively and is useful in respect of efficacy and side effects. Thus, the compound of the present invention can be useful prophylactic and therapeutic drugs for various thrombotic diseases.

We claim:

1. A 3(2H)-pyridazinone of the formula (I):

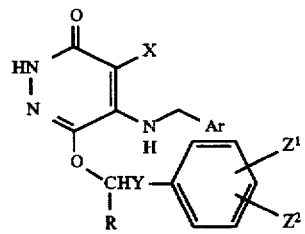

(I)

wherein R is a hydrogen atom or a $C_1$–$C_4$ alkyl group,

X is a hydrogen atom, a chlorine atom or a bromine atom,

Ar is a phenyl group substituted with $OR^1$, wherein $R^1$ is a hydrogen atom or a $C_1$–$C_4$ alkyl group, and A, wherein A is a hydrogen atom, a halogen atom, a $C_1$–$C_4$ alkyl group or $OR^2$, wherein $R^2$ is a hydrogen atom or a $C_1$–$C_4$ alkyl group, Y is $C_1$–$C_8$ alkylene wherein one carbon atom on the straight chain is substituted with one $OR^1$ group, wherein $R^1$ is the same as defined above, and $Z^1$ and $Z^2$ are independently a hydrogen atom, a halogen atom, a $C_1$–$C_4$ alkyl group or a $OR^1$ group, wherein $R^1$ is the same as defined above, or a pharmaceutically acceptable salt thereof.

2. The 3(2H)-pyridazinone according to claim 1, wherein X is a chlorine atom or a bromine atom, or a pharmaceutically acceptable salt thereof.

3. The 3(2H)-pyridazinone according to claim 2, wherein Y is $C_1$–$C_8$ alkylene wherein one carbon atom on the straight chain is substituted with one OH group, $Z^1$ is a hydrogen atom, a halogen atom or a $OR^1$ group wherein $R^1$ is a hydrogen atom or a $C_1$–$C_4$ alkyl group, and $Z^2$ is a hydrogen atom, or a pharmaceutically acceptable salt thereof.

4. The 3(2H)-pyridazinone according to claim 2, wherein Y is $C_1$–$C_4$ alkylene wherein one carbon atom on the straight chain is substituted with one OH group, or a pharmaceutically acceptable salt thereof.

5. The 3(2H)-pyridazinone according to claim 4, wherein A is a hydrogen atom or $OR^2$ wherein $R^2$ is a hydrogen atom or a $C_1$–$C_4$ alkyl group, or a pharmaceutically acceptable salt thereof.

6. The 3(2H)-pyridazinone according to claim 5, wherein $Z^1$ is a fluorine atom, a chlorine atom or a bromine atom, or a pharmaceutically acceptable salt thereof.

7. A method for preparing the 3(2H)-pyridazinone according to claim 1 or a pharmaceutically acceptable salt thereof, which comprises reacting a 5-halo-3(2H)-pyridazinone of the formula (II):

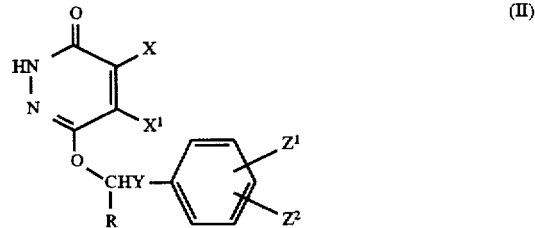

wherein R is a hydrogen atom or a $C_1$–$C_4$ alkyl group,

X is a hydrogen atom, a chlorine atom or a bromine atom, $X^1$ is a chlorine atom or a bromine atom, Y is $C_1$–$C_8$ alkylene wherein one carbon atom on the straight chain is substituted with one $OR^1$ group wherein $R^1$ is a hydrogen atom or a $C_1$–$C_4$ alkyl group, and $Z^1$ and $Z^2$ are independently a hydrogen atom, a halogen atom, a $C_1$–$C_4$ alkyl group or a $OR^1$ group, wherein $R^1$ is the same as defined above, with an arylmethylamine of the formula (III):

wherein Ar is a phenyl group substituted with $OR^1$, wherein $R^1$ is the same as defined above, and A, wherein A is a hydrogen atom, a halogen atom, a $C_1$–$C_4$ alkyl group or $OR^2$, wherein $R^2$ is a hydrogen atom or a $C_1$–$C_4$ alkyl group, or a pharmaceutically acceptable salt thereof, optionally in the presence of a deacidifier.

8. An antiplatelet agent containing an effective amount of the 3(2H)-pyridazinone or a pharmaceutically acceptable salt thereof as defined in claim 1 as an active ingredient.

9. A method for inhibiting platelet aggregation in a subject in need thereof, comprising administering to said subject an antiplatelet effective amount of the 3(2H)-pyridazinone or a pharmaceutically acceptable salt thereof as defined in claim 1.

* * * * *